Figure 5:
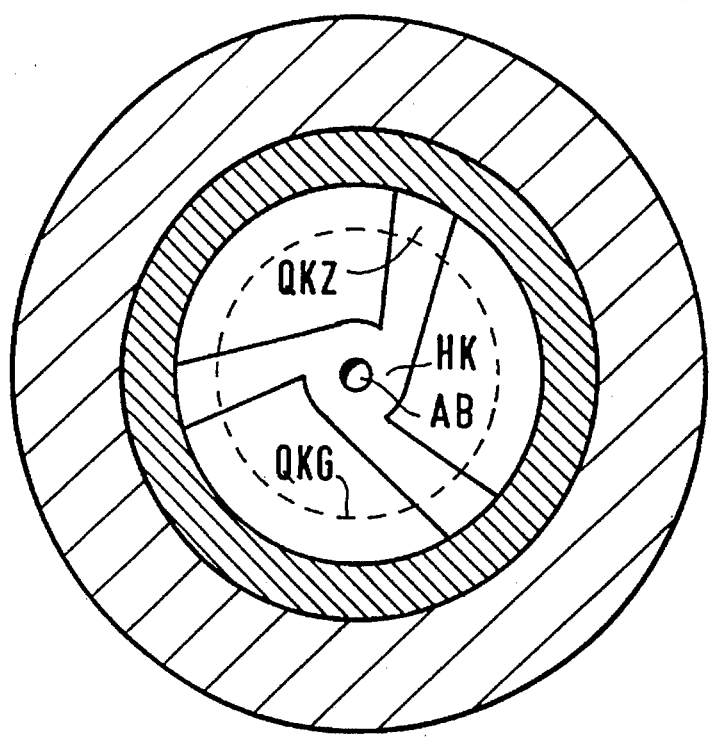

United States Patent [19]
Reidel et al.

[11] Patent Number: 5,605,255
[45] Date of Patent: Feb. 25, 1997

[54] APPARATUS FOR SPRAYING A MIXTURE OF TWO COMPONENTS

[75] Inventors: Guillermo Reidel; Dietmar Weitzel, both of Marburg; Hans Grothoff, Dortmund, all of Germany

[73] Assignee: Behringwerke Aktiengesellschaft, Marburg, Germany

[21] Appl. No.: 494,524

[22] Filed: Jun. 26, 1995

[30] Foreign Application Priority Data

Jun. 28, 1994 [DE] Germany .................. 44 22 505.9

[51] Int. Cl.⁶ .................................................... B67D 5/60
[52] U.S. Cl. .................. 222/137; 222/145.5; 239/432
[58] Field of Search .................. 222/145.5, 145.6, 222/135, 137, 386; 239/303, 304, 329, 399, 432, 491, 492; 604/82, 191

[56] References Cited

U.S. PATENT DOCUMENTS

| | | | |
|---|---|---|---|
| 3,795,364 | 3/1974 | Kattner | 239/432 |
| 4,359,049 | 11/1982 | Redl et al. | 604/191 |
| 4,735,616 | 4/1988 | Eibl et al. | 604/191 |
| 4,978,336 | 12/1990 | Capozzi et al. | 604/191 |
| 4,979,942 | 12/1990 | Wolf et al. | 604/191 |
| 5,033,650 | 7/1991 | Colin et al. | 222/137 |
| 5,116,315 | 5/1992 | Capozzi et al. | 222/137 |
| 5,249,862 | 10/1993 | Herold et al. | 222/137 |

FOREIGN PATENT DOCUMENTS

| | | |
|---|---|---|
| 0037393 | 10/1981 | European Pat. Off. . |
| 0302411 | 2/1989 | European Pat. Off. . |
| 479451 | 4/1992 | European Pat. Off. . |
| 526824 | 2/1993 | European Pat. Off. . |
| 4223356 | 1/1994 | Germany ............ 222/137 |
| 1067717 | 5/1967 | United Kingdom . |

*Primary Examiner*—Andres Kashnikow
*Assistant Examiner*—Philippe Derakshani
*Attorney, Agent, or Firm*—Finnegan, Henderson, Farabow, Garrett & Dunner, L.L.P.

[57] ABSTRACT

The invention relates to an apparatus containing two syringes whose outlets terminate in a spray head with spray nozzle (atomizer). This apparatus is suitable for spraying, and where appropriate applying to a surface, two liquids as mixture. These liquids are preferably the components of an adhesive system, especially of a tissue adhesive.

9 Claims, 3 Drawing Sheets

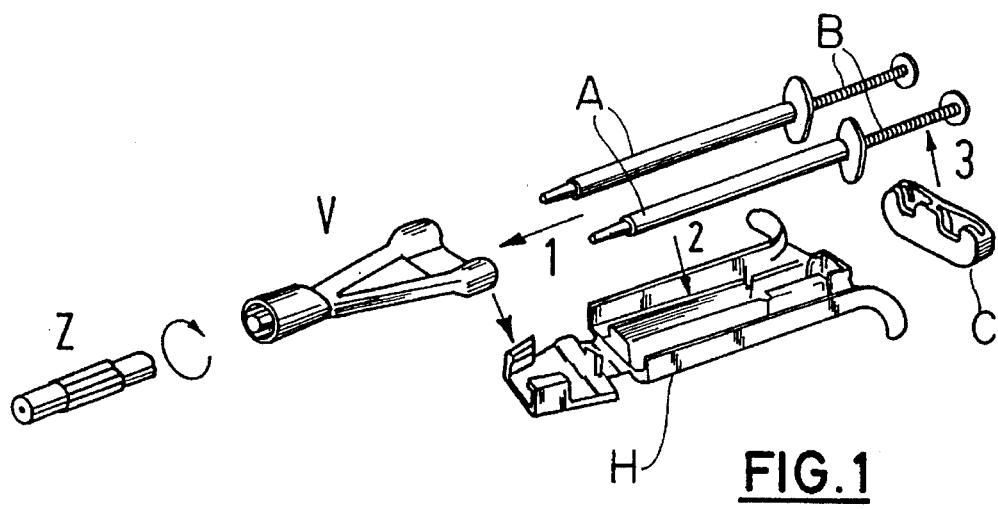
FIG.1
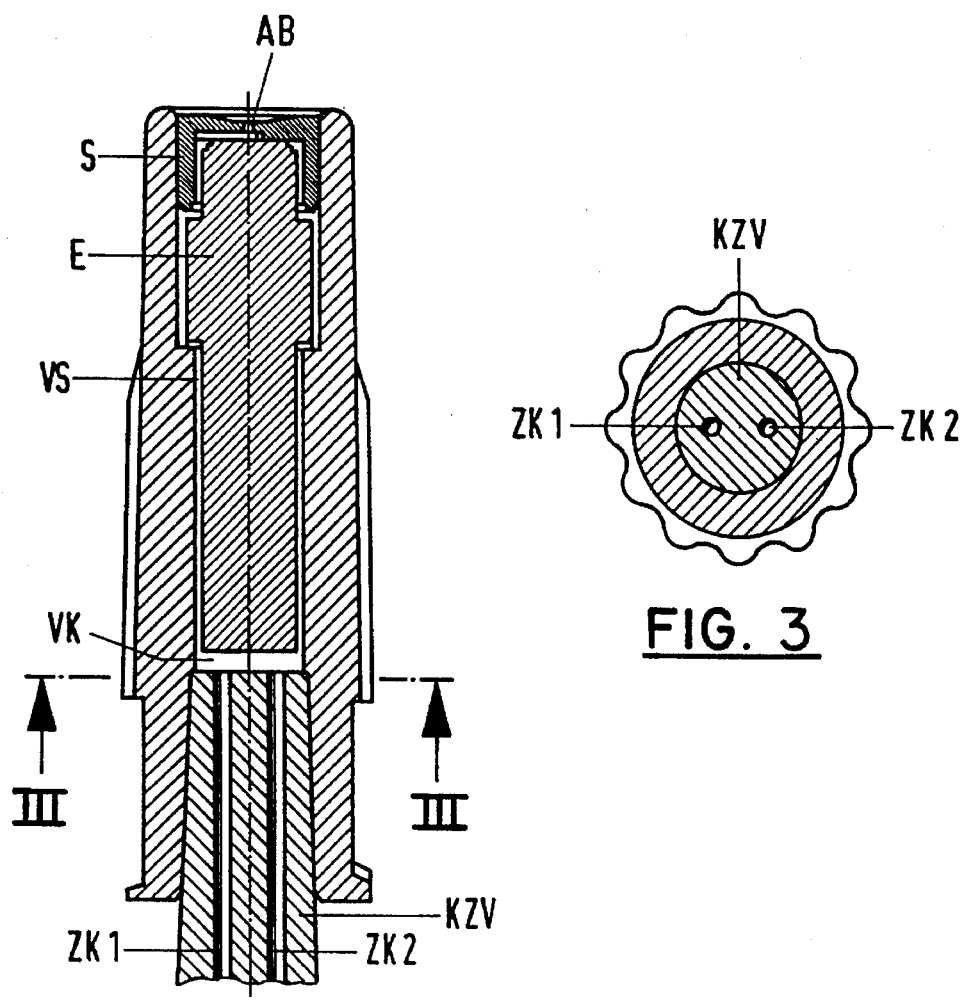
FIG.2
FIG. 3

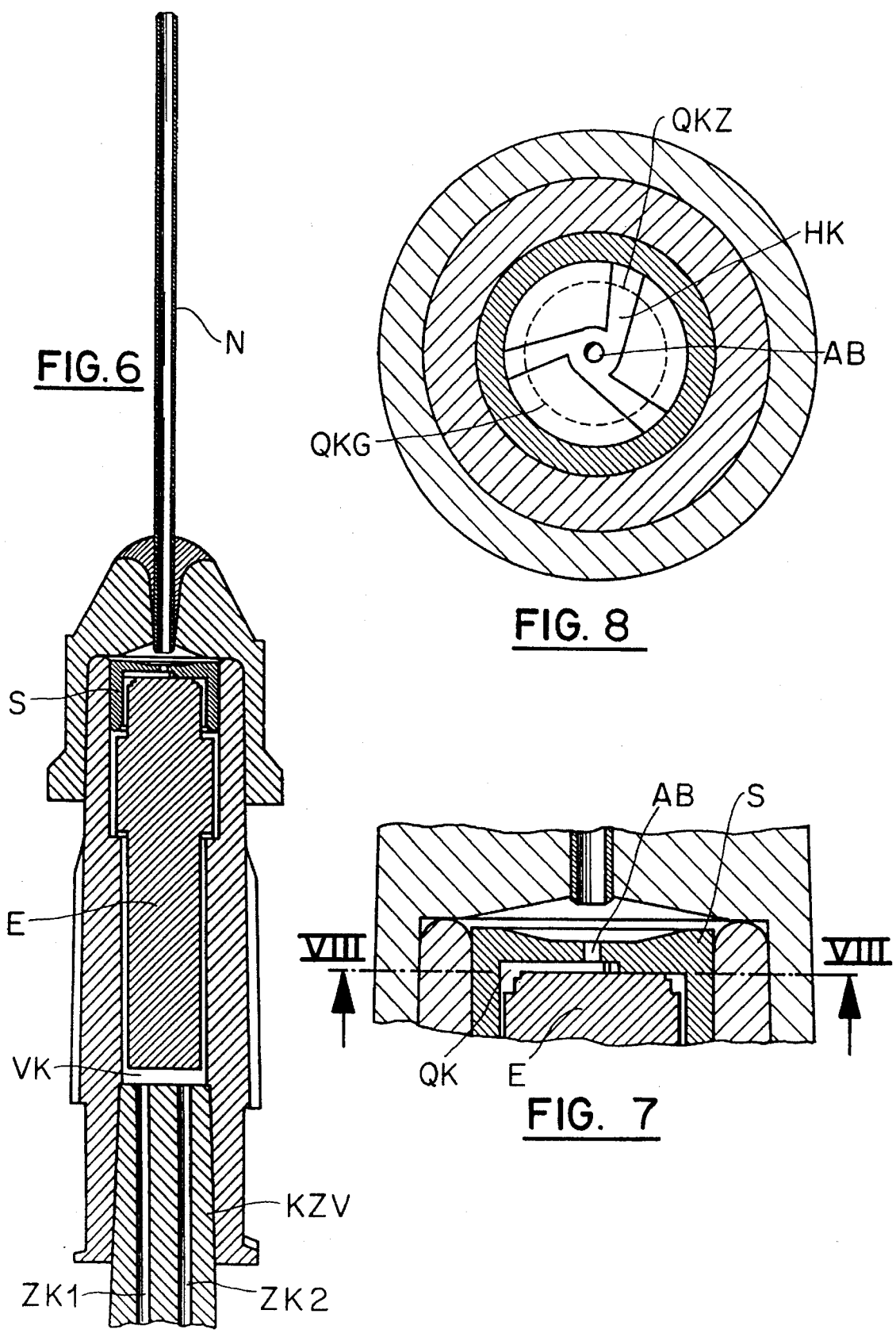

APPARATUS FOR SPRAYING A MIXTURE OF TWO COMPONENTS

FIELD OF THE INVENTION

Apparatus for spraying a mixture of two components The invention relates to an apparatus containing two syringes whose outlets terminate in a spray head with spray nozzle (atomizer). This apparatus is suitable for spraying, and where appropriate applying to a surface, two liquids as mixture. These liquids are preferably the components of an adhesive system, especially of a tissue adhesive.

BACKGROUND OF THE INVENTION

Two-component tissue adhesives which are based on the reaction of fibrinogen with thrombin to form a fibrin clot are, when used on large areas, normally sprayed in order to obtain uniform thin fibrin films. An apparatus in which the administration syringes filled with the components are attached to a spray head is known (EP-A-0,302,411, subsequently referred to as (1)) for this purpose. This spray head has two separate channels for the two components and has a connector, equipped with a Luer Lock, for compressed air, whereby the components can be sprayed by the two syringe pistons being simply pushed forward simultaneously. Despite the good spraying results which can be achieved with this system, the latter is associated with considerable disadvantages on use which have prevented wider application:

- it requires a compressed air or propellant gas connection which is present as a standard in most operating theaters in Germany. However, the standards outside Germany are different and incompatible, or the connections are completely absent;
- it requires a pressure reducer or controller in order to reduce the high pressure of a central compressed air supply to an operating pressure of about 1.5 to 2.5 bar
- the compressed air emerging from the compressed air connection is by its nature non-sterile and must therefore be sterilized by filtration using a special filter;
- the connecting tubing between wall connection and the spray system must be long enough to allow use anywhere. For this reason, they normally tend to be supplied too long so that they can be regarded as traps to trip the operating staff.
- atomization outside the range of the pressure tubing is impossible, which means that the system cannot be used in an ambulance, on outpatients or by non-hospital physicians; and
- assembly of this system is time-consuming and provides various sources of error which may in hospital routine prove to be disturbing and even dangerous.

An apparatus similar to that in (1) is also described in EP-A-0,037,393 (2).

BRIEF SUMMARY OF THE INVENTION

The object of this invention was to provide a system which does not have these disadvantages.

Figure 4:
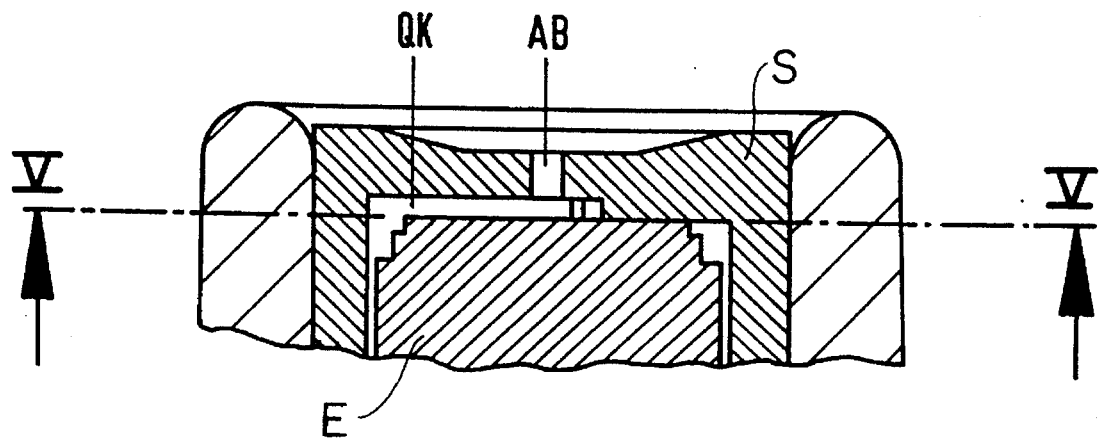

It is evident from the two said publications (1) and (2) as an essential indicator that there is a need for thorough mixing of the two components. The disadvantages of (2) in this direction have been adequately described in (1). However, even (1) also displays considerable disadvantages in this point, besides the general disadvantage of the dependence on compressed air. Thus, the deficiency, which is emphasized by (1) comparing with (2), of insufficiently thorough mixing of the Components is not eliminated by (1) either. Although (1) has evidently reduced the problem of the dependence on distance (intersection point orientation) of (2), it has nevertheless in the final analysis not brought about any essential improvement in the accuracy of mixing and the degree of homogenization. Instead, it is found that the mixing ratio of the components to one another, measured by the total area of the spray produced, varies extremely widely. The individual components are to be found in unmixed form in particular in the edge regions of the sprayed area, as can also be inferred from FIG. 4 (1). The further the component portions are from the separating bar, the less intensively they are involved in the mixing process. This adverse effect is further enhanced at low spray distances and furthermore depends on the pressure of compressed air. The result which is obtained is thus by no means satisfactory in practice. Besides the inconvenient handling owing to the additional supplying of compressed air, the inhomogeneity of the mixture results in both the strengths and adhesions of the bondings and sealings produced, and the surface properties of the films, being not optimal.

The invention avoids the disadvantages and difficulties described above and has the object of producing an apparatus which ensures that, even before the actual emergence of the components, inside the apparatus there is both accurate adjustment of the prescribed mixing ratio of the components to one another, and uniform mixing of the components with one another, and it ought to be possible to carry out this process and the actual administration purely by hand and without the aid of additional energy, whereby influencing by external factors or by manipulations can be very substantially excluded.

The object is achieved according to the invention by individual components being metered through two or more commercially available syringe bodies, which are coupled together in terms of movement and outlets, into a premixing chamber and from there, after passing through a premixing section, pass through a plurality of transverse channels into a homogenization chamber where final mixing of the individual streams and homogenization of the individual components takes place, and actual administration taking place only after leaving the homogenization chamber.

Atomizers for manual spraying of cosmetics, cleaners and other liquids without use of compressed or propellant gas are known.

The spraying of two-component tissue adhesives without use of compressed or propellant gas, with a mixing and, associated therewith, with initiation of the polymerization reaction of the components even before leaving the spray element has been regarded hitherto as impossible. On the one hand, the components, in particular the fibrinogen concentrate, are highly viscous protein solutions and, on the other hand, the components react vigorously with one another on mixing, with coagulation starting within a few seconds (about 4–5 sec) so that has been necessary to worry about blockage of the spray nozzle.

A thrombin product which can be sprayed for local hemostasis using a simple, sterile atomizer which is included in the pack is known in the USA. This is possible without complications in the case of thrombin solutions because they are used as inert, low-viscosity solution so that the spray nozzle cannot become blocked.

However, this atomizer is unsuitable for tissue adhesives. The adhesive cannot be sprayed, since the spray nozzle becomes blocked within a short time.

It has been possible to develop an atomizer (spray head with spray nozzle) in which it has been possible to reduce the dead volume and thus the loss of valuable substance to a minimum. This has made it possible to shorten the residence time of the mixed components in the atomizer so that, under normal conditions, no blockage of the spray nozzle is observed. This system avoids the disadvantages of the stationary systems.

In addition, the spray head with spray nozzle according to the invention can easily be exchanged if on administration there is interruption for a lengthy period and renewed spraying is no longer possible.

BRIEF DESCRIPTION OF THE DRAWINGS

FIG. 1 is an exploded perspective view of an atomizer according to the invention attached to a two-component adhesive apparatus.

FIG. 2 is a sectional view of the atomizer head.

FIG. 3 is a view of the atomizer head in cross-section.

FIG. 4 is a sectional view of the spray nozzle of the atomizer.

FIG. 5 is a cross-sectional view showing the channels of the spray nozzle.

FIG. 6 illustrates the atomizer having a syringe needle attached.

FIG. 7 is a sectional view of the spray nozzle in FIG. 6.

FIG. 8 is a cross-sectional view along line VIII—VIII in FIG. 7.

DETAILED DESCRIPTION OF THE PREFERRED EMBODIMENTS

The invention additionally considerably reduces the resulting plastic waste.

Mode of operation of the apparatus for the example of the preferred embodiment:

The invention relates to an apparatus for spraying two liquids as mixture, where this apparatus contains two syringes A to receive the liquids, whose outlets are connected to a connecting piece which brings the two liquids together and terminates in a spray head with spray nozzle. The two liquids are preferably the components of a two-component adhesive, in particular of a fibrinogen-based tissue adhesive. A preferred embodiment is depicted in FIGS. 1–5. However, the invention also of course relates to equivalent embodiments.

For bonding tissues using two-component adhesives, normally first the 2 components are prepared by the components, which are in solid form, being dissolved in the particular solvent and drawn up into the administration syringes shortly before use.

The syringes filled with fibrinogen solution and thrombin solution obtained in this way are fitted into the apertures, provided for this purpose, in the Y-shaped connecting piece V (see FIG. 1, step No. 1) and inserted into the conical recess in the syringe holder H. The syringes are then locked into the syringe holder H (step No. 2). The syringe plungers B are then connected to the gripping plate C (step No. 3) so that canting of the syringe plungers is prevented. Finally, the atomizer Z (spray head with spray nozzle) provided for example with Luer Lock connection is screwed or fitted onto this system (step No. 4).

For the spraying, the contents of the administration syringes are pushed, from a distance of about 10 to 20 cm from the object to be sprayed, with a continuous uniform pressure of the thumb on the gripping plate, through the two working channels of the Y-shaped connecting piece, mixed in the premixing chamber of the atomizer (spray head with spray nozzle), and driven through the narrowing of the cross-section of the lumen caused by the insert or inserts (E) at an increasing rate as far as the outer spray nozzle (S). The tissue adhesive leaves the spray nozzle as a fine, uniform mist and covers the tissue as a fine film.

If the atomizer (spray head with spray nozzle) becomes blocked due to an interruption in administration, it can easily be replaced by a new one.

In another advantageous application, the spray head with spray nozzle (atomizer) is used as homogenizing apparatus for administration by means of a needle N attached to the spray nozzle. This makes it possible to apply the tissue adhesive in a targeted manner to small bonding sites, and the bonding action has a very rapid onset because of the thorough mixing.

This is advantageous on use because the apparatus can then be supplied with the spray head, containing the spray nozzle, already fitted and, after insertion of the filled syringe bodies, can be immediately employed for the spray application without further fitting. In the case of administration by needle, the latter is then merely attached in addition. Since this exchange process can be carried out very quickly it is possible during an application to switch from one to another administration form without the need to worry about the components being cured too much for further use and blocking the syringe pistons because the spray nozzle is blocked.

Further details are shown in FIGS. 1–8, in particular the advantageous effects of the insert:

reduction in the dead volume limitation of the nozzle insertion depth premixing function by multiple reversal of the volume flow covering of the homogenization chamber and partial covering of the transverse channels.

We claim:

1. An apparatus for spraying a liquid mixture comprising:

first and second syringes, each having an outlet for supplying first and second liquids;

a connecting piece having first and second channels in communication with said first and second syringe outlets;

said first and second channels terminating at a premixing chamber for premixing the first and second liquids to form a mixture;

a reduced volume section downstream from said premixing chamber, said reduced volume section terminating in a homogenization region for homogenizing the liquid mixture; and an exit aperture for spraying the liquid mixture.

2. The apparatus of claim 1, wherein said syringes are removably positioned in a syringe holder.

3. The apparatus of claim 1, wherein said first and second syringes further comprise first and second plungers, said first and second plungers being connected to a single gripping plate.

4. The apparatus of claim 1, wherein said premixing chamber, reduced volume section, and homogenization region are contained within a spray head removably attached to said connecting piece.

5. The apparatus of claim 1, wherein said reduced volume section is formed by an insert which separates said premixing chamber and homogenization region.

6. The apparatus of claim 1, wherein said reduced volume section and said homogenization region are separated by a plurality of transverse channels.

7. The apparatus of claim 1, wherein said first and second syringes are filled with first and second components of a multi-component adhesive.

8. The use of the apparatus of claim 1, wherein said apparatus is used to apply a multi-component adhesive.

9. The use as claimed in claim 8, wherein said multi-component adhesive is a tissue adhesive.

* * * * *